United States Patent [19]

Simon et al.

[11] Patent Number: 5,296,354
[45] Date of Patent: Mar. 22, 1994

[54] KIT FOR THE SPECIFIC ASSAY OF ANGIOTENSIN II

[75] Inventors: Dominique Simon; Jean Marchand, both of Montpellier; Gabriel Badouaille, Pignan; Bernard Romestand, Saint-Gely-du-Fesc; Jean-Alain Fehrentz, Saint Nazair du Pezan, all of France

[73] Assignee: Elf Sanofi, Paris, France

[21] Appl. No.: 726,376

[22] Filed: Jul. 5, 1991

[30] Foreign Application Priority Data

Jul. 5, 1990 [FR] France .................. 90 08563

[51] Int. Cl.⁵ ........................... G01N 33/53
[52] U.S. Cl. .................. 435/7.92; 530/387.9; 530/388.24; 530/389.2; 436/548
[58] Field of Search ........... 435/7.9, 7.91, 7.92, 435/7.93, 962; 530/387, 316, 387.9, 388.24, 389.2; 436/548, 815, 808

[56] References Cited

U.S. PATENT DOCUMENTS 4,772,685  9/1988  Schmidt et al. ............... 530/806
4,911,909  3/1990  ............................... 424/858

FOREIGN PATENT DOCUMENTS 0273453  6/1988  European Pat. Off. .

OTHER PUBLICATIONS

Nussberger, J. et al. Selectivity of Angiotensin II Antisera J. of Immunol. Methods 56(1983):85–96.
Couraud, Pierre-Oliver Structural Analysis of the Epitopes Recognized by Monoclonal Antibodies to Ang II, J. of Immunol. 136(9):3365–70.
Aikawa, Tadaomi et al. Enzyme Immunoassay of Ang I Endocrinol. 105(1):1–6 (1979).
Takai, E. et al. a solid-phase enzyme immunoassay for determination of IgM and IgG Ab against translation products of pre-S1 and pre-S2 regions of hepatitis B virus-J. Immunol. Meth. 23:23–30 (1986).
Nussberger, J. et al., "A Simplified Radioimmunoassay for Physiologically Active Agniotensin Peptides [(1–8) Octa-and (2–8) Heptapeptides]", Horm. metabol. Res. 16 (1984):606–610.

Primary Examiner—Esther L. Kepplinger
Assistant Examiner—Donna C. Wortman
Attorney, Agent, or Firm—Foley & Lardner

[57] ABSTRACT

The present invention relates to a kit for the specific assay of Angiotension II, comprising:
the anti-Ang II antibody,
a solution of labelled Ang II,
solutions containing the Ang II standards at known and increasing concentrations,
the requisite washing solution(s),
a solution of anti-Ang III antibody, the said antibody exhibiting a cross-reaction with Ang II of less than 10% and preferably less than 5%,
and, optionally, a solution of anti-Ang I antibody and/or a solution of anti-pentapeptide antibody and/or a solution of anti-hexapeptide antibody, the said antibodies exhibiting a cross-reaction with Ang II of less than 10% and preferably less than 5%.

49 Claims, No Drawings

KIT FOR THE SPECIFIC ASSAY OF ANGIOTENSIN II

The present invention relates to a kit for the specific immunoassay of angiotension II and to the method for the immunoassay of angiotension II using the said kit.

Angiotension II is a potent vasopressor agent which is the biologically active product of the renin-angiotension system: renin acts on the angiotensinogen of the plasma to produce a decapeptide (1-10), angiotensin I, the latter is converted to an octapeptide (1-8), angiotensin II, by the action of the converting enzyme and an aminopeptidase then produces a heptapeptide (2-8): angiotensin III.

The formulae of these different peptides in mammals are given below:

Angiotensin I, hereinafter designated Ang I (SEQUENCE ID NO. 1):

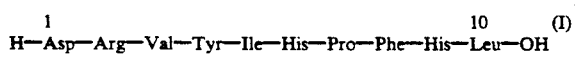

Angiotensin II, hereinafter designated Ang II (amino acids 1-8 of SEQUENCE ID NO. 1):

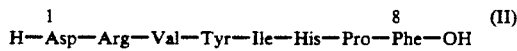

Angiotensin III, hereinafter designated Ang III (amino acids 2-8) of SEQUENCE ID NO. 1):

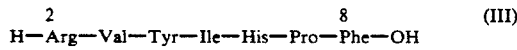

A recent publication has shown that Ang III is itself degraded to two peptides (D. J. CAMBELL et al., J. Hypertens., 1990, 8, 165-172). Among these degradation peptides, special mention may be made of a hexapeptide of formula (amino acids 4-8 of SEQUENCE ID NO. 1):

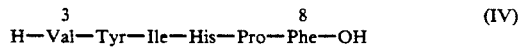

hereinafter designated hexapeptide IV, and a pentapeptide of formula (amino acids 4-8 of SEQUENCE ID NO. 1):

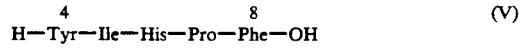

hereinafter designated pentapeptide (V).

These degradation peptides are present in human plasma. It is probable that they are also to be found in the plasma of other mammals.

Exploration of the hormonal aspects of the renin-angiotensin system is very important for the diagnosis and treatment of arterial hypertension. At the present time, this exploration performed in the clinical situation is limited to measurement of the enzymatic activity of plasma renin and of the activity of the converting enzyme and to measurement of the plasma concentration of active renin.

The direct assay of Ang II, which is the active peptide of the system, is difficult to carry out for several reasons:

very low plasma concentration of Ang II (3 to 20 pg/ml in normal subjects, equivalent to $3 \times 10^{-12}$ to $2 \times 10^{-11}$M), which necessitates the use of a very high-affinity anti-Ang II antibody structural similarity of Ang II to various peptides derived from the cleavage of angiotensinogen and present in plasma, especially Ang I and above all Ang III or other degradation peptides which can interfere in the assay.

Thus, J. NUSSBERGER et al. describe a radioimmunoassay which does not permit a distinction to be made between Ang II and III in human plasma (Hormon. Metab. Res., 1984, 16 (II), 606-610 and J. Hypertens., suppl., 1988, 6 (4), S424-S425). Moreover, European Patent Application 273,453 describes several anti-Ang II monoclonal antibodies, all of which exhibit a cross-reactivity with Ang III; the lowest cross-reactivity, observed with one of them, is 32%. Thus, the reaction of Ang II with this antibody is not specific.

Furthermore, this monoclonal antibody has a low affinity, of the order of $10^9 M^{-1}$, which is insufficient to permit an assay in plasma (Biochem. Biophys. Res. Commun. 1987, 143, p. 133-139).

The anti-Ang II antibody referred to as 4D8 and described in the proceedings of the Congress "The Renin-Angiotensin System as a Therapeutic Target" Basle, 29-31 Oct. 1989, a SANOFI communication, possesses a strong affinity of the order of $10^{-11}M^{-1}$; but it exhibits a cross-reactivity of the order of 100% with Ang III and with the hexapeptide (IV); it exhibits an approximately 50% cross-reactivity with the pentapeptide (V). In fact, it is very difficult, and unknown at the present time, to have an antibody both with a very high affinity for Ang II and not exhibiting a cross-reaction with Ang III and the degradation peptides.

Moreover, the specific assay of Ang II presents, at the present time, a methodological problem which necessitates performing several steps in succession on the blood sample (J. NUSSBERGER et al., Hypertension, 1986, 8, 476-482):

1. an extraction of the different angiotensins and of the degradation peptides to prepare a plasma extract containing them,
2. a separation by high performance liquid chromatography (HPLC) of the different angiotensins derived from the metabolism of angiotensinogen and present in plasma,
3. a radioimmunoassay of the fractions collected after elution.

Extraction of the angiotensins from the plasma is an essential step common to all the techniques of assay of Ang II; it is performed by chromatography on a silica column according to the method described by J. NUSSBERGER et al. in Hypertension, 1985 (7), suppl. 1, I-1-I-7.

As a result of the step of separation by HPLC, this technique is cumbersome and tedious to carry out; for this reason, it cannot be used to assay a large number of plasma samples under routine conditions.

An attempt has been made to develop a specific assay for Ang II, enabling the level of Ang II to be measured accurately irrespective of the concentrations of Ang I, Ang III and the degradation peptides present in the medium, and which can be carried out in a time compatible with routine clinical use. Such a specific assay is of great interest:

either for studying the physiology of the renin-angiotensin system in different animal species in experimental situations, or for diagnosing pathological situations in man, or for the diagnosis and monitoring of treatments for arterial hypertension.

Generally, Ang II is assayed from plasma. It is possible, according to the present invention, to carry out the assay of Ang II either in plasma or in any other biological fluid in which it is present.

The assay according to the invention may be performed with any animal species in which it is desired to find out the specific measurement of Ang II, and more especially in man.

According to the present invention, it has been found that a specific immunoassay of Ang II may be performed by using simultaneously an antibody directed towards Ang II, intended for the actual assay, and an antibody specific for Ang III as well as, optionally, one or more antibodies each specific for Ang I or for a degradation peptide. Antibody specific for Ang III and antibody specific for Ang I or for a degradation peptide are understood to mean antibodies each exhibiting a cross-reaction with respect to Ang II of less than 10%. Thus, the Ang III and, optionally, the Ang I and the degradation peptides, each captured by a specific antibody, are in practice no longer available to give cross-reactions with the anti-Ang II antibody. The Ang II assay thus becomes completely specific, that is to say completely free from all interference due to the presence of related peptides in the sample.

According to the present invention, the measurement of Ang II entails only two steps:

1. extraction of the different angiotensins and of the degradation peptides to prepare the extract of biological fluid containing them,
2. the actual immunoassay of the Ang II contained in the said extract.

Thus, the separation by HPLC of the different angiotensins in the extract is avoided, this step being the slowest and most laborious of the protocol for specific assay of Ang II.

The immunoassay used is a competitive assay: labelled Ang II bound to the anti-Ang II antibody is displaced by the unlabelled Ang II contained in the sample to be assayed. Reference to a calibration curve, established with standards containing known quantities of Ang II, enables the Ang II concentration present in the sample to be determined.

The Ang II is labelled either with a radioelement such as tritium ($^3$H) or iodine-125 ($^{125}$I), or with an enzyme such as, for example, acetylcholinesterase, peroxidase, alkaline phosphatase or $\beta$-galactosidase, or with a fluorescent label, or with a luminescent label.

According to the present invention, an antibody specific for Ang III and, optionally, one or more antibodies each specific for Ang I or for a degradation peptide, which mask the Ang III and, optionally, the Ang I and the degradation peptides present in the sample by formation of the corresponding antigen-antibody complex(es), are added to the reaction medium. The appearance of cross-reactions between the Ang III and, optionally, the Ang I and the degradation products, present in the sample, with the anti-Ang II antibody is thereby avoided.

The subject of the present invention is also a kit for the specific assay of Ang II, comprising:

the anti-Ang II antibody, a solution of labelled Ang II, solutions containing the Ang II standards at known and increasing concentrations, the requisite washing solution(s), a solution of anti-Ang III antibody, the said antibody exhibiting a cross-reaction with Ang II of less than 10% and preferably less than 5%, and, optionally, a solution of anti-Ang I antibody and/or a solution of anti-hexapeptide (IV) antibody and/or a solution of anti-pentapeptide (V) antibody, the said antibodies exhibiting a cross-reaction with Ang II of less than 10% and preferably less than 5%.

When the Ang II is labelled with an enzyme, the kit comprises, in addition:

a solution containing the substrate for the said enzyme and, optionally one or more reagents necessary for visualising the activity of the enzyme, a solution intended for stopping the enzymatic reaction.

The anti-Ang II antibody used in the assay kit can be polyclonal or monoclonal; it may be used in solution or bound to a solid support. As solid supports, tubes, microtitration plates and particles, magnetic or otherwise, may be mentioned.

According to the present invention, the preferred anti-Ang II antibody is monoclonal; advantageously, it is bound to a solid support, according to methods well known to those skilled in the art.

The anti-Ang III antibody can be a polyclonal antibody or a monoclonal antibody. The same applies to the anti-Ang I, anti-hexapeptide (IV) and anti-pentapeptide (V) antibodies.

When the antibodies used are in solution, the appropriate dilution for each of the peptides, present in the sample to be assayed, to be captured by the corresponding anti-peptide antibody is determined prior to the assay.

The subject of the present invention is also the method in which the assay kit according to the invention is used. The said method is characterised in that it comprises the following steps:

a) the reaction medium comprising the following is prepared:

the extract of biological fluid to be assayed, the anti-Ang II antibody, the labelled Ang II, the anti-Ang III antibody, and, optionally, the anti-Ang I antibody and/or the anti-hexapeptide (IV) antibody and/or the anti-pentapeptide (V) antibody;

b) the reaction media useful for the calibration, each comprising the following, are prepared simultaneously:

an Ang II standard, the anti-Ang II antibody, the labelled Ang II, the anti-Ang III antibody, and, optionally, anti-Ang I antibody and/or the anti-hexapeptide (IV) antibody and/or the anti-pentapeptide (V) antibody;

c) the media are left to incubate at a temperature between 4° C. and room temperature for 12 to 72 hours;

d) the Ang II bound to the anti-Ang II antibody is separated from the free Ang II;

e) lastly, the reading of the results is performed according to a suitable method.

Preferably, the method according to the invention is used for the specific assay of Ang II in a plasma extract.

When the anti-Ang II antibody is used in solution, steps a) and b) are carried out by mixing:

25 to 500 µl of extract of biological fluid to be assayed, or of Ang II standard, with a medium containing:
25 to 500 µl of solution of anti-Ang II antibody,
25 to 500 µl of solution of anti-Ang III antibody,
optionally, 25 to 500 µl of solution of anti-Ang I antibody and/or 25 to 500 µl of anti-hexapeptide (IV) antibody and/or 25 to 500 µl of anti-pentapeptide (V) antibody, and
25 to 500 µl of solution of labelled Ang II.

It is possible, where appropriate, to perform a 3- to 24-hour preincubation before adding the solution of labelled Ang II.

Step d) is carried out by a conventionally used separating method:
either by immunological binding using antibodies directed towards the immunoglobulins of the animal species to which the anti-Ang II antibody used belongs, these antibodies themselves being insolubilised on a solid phase (insoluble support such as, for example, tubes, microtitration plates or particles, magnetic or otherwise),
or by physicochemical precipitation of the antigen-antibody complex using a precipitating agent such as polyethylene glycol,
or by separation of the free antigen with the charcoal-dextran complex (J. NUSSBERGER et al., J. Lab. Clin. Med., 1984, 103 (2), 304–312).

When, according to another embodiment of the method according to the invention, the anti-Ang II antibody is bound to a solid support, the preparation of the reaction medium (steps a and b) is performed in the presence of the said support. It is possible, for example, to use tubes coated with anti-Ang II antibodies in which the following are mixed:
25 to 500 µl of extract of biological fluid to be assayed or of Ang II standard,
25 to 500 µl of solution of anti-Ang III antibody,
optionally, 25 to 500 µl of solution of anti-Ang I antibody and/or 25 to 500 µl of anti-hexapeptide (IV) antibody and/or 25 to 500 µl of anti-pentapeptide (V) antibody, and
25 to 500 µl of solution of labelled Ang II.

According to this embodiment of the method according to the invention, the separation (step d) is carried out by aspiration of the incubation solution from the reaction medium, followed by washing and further aspiration in order to remove Ang II which is not complexed by the antibody bound to the solid support. It is also possible to prepare the mixture described above in a normal tube or vessel and to add the anti-Ang II antibody in the form of particles, magnetic or otherwise, to which the anti-Ang II antibody is bound. In this case, the separation (step d) is carried out according to the same principle as above, but by application of a method enabling the particles to be retained (centrifugation, filtration, use of a magnet where magnetic particles are involved).

In all cases, the reading step e), which is applied to the solid phase in which the anti-Ang II antibody complexing the Ang II to be assayed is included, or to which this antibody is bound, is then performed directly.

Generally speaking, the reading step depends on the method of labelling used for the Ang II. Thus:
either a measurement of radioactivity, when radiolabelling has been used,
or a measurement of absorbance or of light emission, when fluorescent or luminescent labelling or enzyme labelling, depending on the nature of the enzyme and substrate employed, has been used, is performed.

In the description which follows and in the claims, the amino acids are named using the abbreviations recommended by the IUPAC; in addition, the following abbreviations are used:
BOP  benzotriazolyloxytris(dimethylamino)phosphonium hexafluorophosphate
Boc: tert-butoxycarbonyl
Mob: para-methoxybenzyl
DCB: 2,6-dichlorobenzyl
Tos: tosyl
MAb: monoclonal antibody
BSA: bovine serum albumin
BGG: bovine gamma-globulin
cpm: counts per minute
PEG: polyethylene glycol
LPH: Limulus polyphemus haemocyanin
Sulpho-MBS: N-(3-maleimidobenzoyloxy)sulphosuccinimide sodium salt
Bo: concentration of the (labelled Ang II)-anti-Ang II antibody complex in the absence of unlabelled Ang II or unlabelled Ang III,
B: concentration of the (labelled Ang II)-anti-Ang II antibody complex for each concentration of unlabelled Ang II or unlabelled Ang III.

Lastly, another subject of the present invention is the preparation of anti-Ang III antibodies.

The anti-Ang III antibody is prepared in a conventional manner by immunisation of an animal with an immunogen. Said immunogen consists of a peptide derivative bound to a modified protein or carrier protein (see Am. J. Obstet. Gyneco. 1972, 113, p. 751–757). As examples of animals capable of being used in this method, rabbits, goats, sheep, rats and mice may be mentioned.

The monoclonal antibodies are obtained by the method of Kohler and Milstein which is well known to those skilled in the art.

In the same manner, anti-Ang I, anti-hexapeptide (IV) and anti-pentapeptide (V) antibodies may be prepared.

The use of a carrier protein in the immunisation in relation to molecules of low molecular weight (hapten) enables the formation of specific anti-hapten antibodies to be induced in the animal.

The most widely used carrier proteins are, at the present time, albumins of animal origin (commercially available, stable, highly immunogenic). The synthesis of the protein-peptide conjugate is carried out by the formation of a thioether type covalent bond between the thio group of the peptide and the maleimide group of the protein, introduced beforehand by reaction with sulpho-MBS.

According to the present invention, the peptide derivative chosen as an immunogen for preparing the anti-Ang III antibody corresponds to the formula (SEQUENCE ID NO. 2):

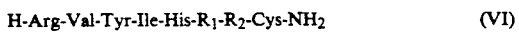

H-Arg-Val-Tyr-Ile-His-$R_1$-$R_2$-Cys-$NH_2$ (VI)

in which
$R_1$ denotes a direct bond or a chain-link comprising 1 or 2 natural amino acids. Preferably, $R_1$ represents -Pro- or —Pro- bound to another natural amino acid;
$R_2$ represents a group of formula: —NH—$(CH_2)_n$—CO— in which n varies between 1 and 9; preferably n is 5.

Thus, according to the present invention, the preferred anti-Ang III antibody is the antiserum obtained by immunisation of an animal with the immunogen consisting of the peptide (VI) bound to a carrier protein.

More especially preferred is the antiserum obtained with the immunogen consisting of the peptide of formula (6-aminohexanoic acid species of SEQUENCE ID NO. 2):

H-Arg-Val-Tyr-Ile-His-R'₁-Ahx-Cys-NH₂ in which $R'_1$ represents -Pro- or Pro- bound to another amino acid and Ahx denotes a 6-aminohexanoic acid residue, the said peptide being carried by bovine serum albumin modified with sulpho-MBS. When the animal is a rabbit, the antiserum thereby obtained exhibits a cross-reaction with Ang II of less than 1%.

Likewise, according to the present invention, the peptide derivative chosen as an immunogen for preparing the anti-Ang I antibody corresponds to the formula (SEQUENCE ID NO. 3):

H-Cys-R₂-R₃-Arg-Val-Tyr-Ile-His-Pro-Phe-His-Leu-OH  (VII)

in which:
$R_3$ denotes a direct bond or a chain-link comprising 1 or 2 natural amino acids. Preferably, $R_3$ represents Asp or Asp bound to another natural amino acid;
$R_2$ has the meaning stated above for (VI).

According to the present invention, the peptide derivative chosen as an immunogen for preparing the anti-hexapeptide antibody corresponds to the formula (amino acids 2-8 of SEQUENCE ID NO. 2):

H-Val-Tyr-Ile-His-R₁-R₂-Cys-NH₂  (VIII)

in which $R_1$ and $R_2$ have the meanings stated above for (VI).

Lastly, according to the present invention, the peptide derivative chosen as an immunogen for preparing the anti-pentapeptide antibody corresponds to the formula (amino acids 3-8 of SEQUENCE ID NO. 2):

H-Tyr-Ile-His-R₁-R₂-Cys-NH₂  (IX)

in which $R_1$ and $R_2$ have the meanings stated above for (VI).

In the definitions of $R_1$, $R'_1$ and $R_3$, the other natural amino acid may be chosen from the following amino acids: Ala, Val, Leu, Ile, Pro, Phe, Trp, Met, Ser, Thr, Cys, Tyr.

Thus, according to the present invention, the antibodies are obtained by immunisation of an animal with a peptide derivative of formula (VII) or a peptide derivative of formula (amino acids 1-7 or 2-7 or 3-7 of SEQUENCE ID NO. 2):

H-X₁-Tyr-Ile-His-R₁-Cys-NH₂ in which:
$R_1$ denotes a direct bond or a chain-link comprising 1 or 2 natural amino acids. Preferably, $R_1$ represents -Pro- or —Pro- bound to another natural amino acid;
$R_2$ represents a group of formula —NH—(CH₂-)ₙ—CO— in which n varies between 1 and 9; preferably n is 5, and characterised in that:
when $X_1$ represents a direct bond, the antibody is specific for the pentapeptide,
when $X_1$ represents a valine residue, the antibody is specific for the hexapeptide,
when $X_1$ represents a residue of the dipeptide Arg-Val, the antibody is specific for angiotensin III.

The antibodies according to the invention exhibit a cross-reaction with Ang II of less than 10% and preferably less than 5%.

The above peptide derivatives employed for the production of the antibodies according to the invention constitute another subject of the invention.

Said peptides are prepared by conventional peptide synthesis methods, notably by the so-called step-wise process, preferably in solid phase.

The invention will now be described in greater detail by means of the illustrative examples below.

EXAMPLE 1

Preparation of anti-Ang III.

A) Preparation of the peptide (VI) in which $R_1$=Pro and $R_2$=Ahx.

The compound VI was synthesised in the solid phase using methods known in peptide chemistry.

The solid phase used is 4-methylbenzhydrylamine resin functionalised to a level of 0.4 mmol per gram. The successive condensation of amino acids is performed with the BOP reagent; the alpha-amino functions are protected temporarily with a Boc group and deprotected with a trifluoroacetic acid/dichloroethane/ethanedithiol (35:70:5 v/v/v) solution. The side chains of the different amino acids are protected with suitable groups: Mob for Cys, Boc for His, DCB for Tyr, Tos for Arg.

Once synthesised, the peptide is deprotected and separated from the resin by the action of hydrofluoric acid containing 10% of anisole for 1 hour at 0° C. The peptide is then precipitated with ether, taken up with an acetonitrile/water/trifluoroacetic acid (60:40:0.1 v/v/v) solution and lyophilised. Purification is performed by liquid chromatography under pressure on a reversed-phase column.

The various analytical results are in agreement with the expected structure for the peptide (VI).

B) Preparation of the modified protein (LERNER, R. A. et al. (1981) Proc. Nat. Acad. Sci. USA, 78, 3403-3407).

The protein chosen for binding the peptide (VI) is bovine serum albumin (BSA) modified by reaction with sulpho-MBS.

22.4 mg of solid sulpho-MBS (Pierce) are added to a solution of 4 ml of BSA (containing 10 mg/ml) in 0.05M potassium phosphate buffer pH 8.0, equivalent to a stoichiometry of 80MBS/BSA equivalents. The reaction is allowed to proceed for 1 hour at room temperature with . gentle stirring and the mixture is then dialysed for 18 hours at 4° C. against 2 liters of 0.1M phosphate buffer pH 7.0.

Determination of the degree of substitution is carried out by measuring the number of maleimide groups introduced by means of reaction with cysteine radiolabelled with ¹⁴C. 0.6 ml of 0.1M phosphate buffer pH 7.0 and 0.05 ml of 20 mM cysteine to which ¹⁴C has been added (final concentration 3 kBq/μmol of cysteine) are added to 0.4 ml of reaction medium. After incubation for 1 hour 30 minutes at 30° C. followed by filtration of the reaction medium through a chromatography column under suitable conditions, measurement of the radioactivity enables the observed degree of modification to be calculated, which is 11 maleimide groups per mol of BSA.

C) Coupling of the peptide (VI).

5 mg of peptide (VI) prepared above are dissolved in 0.25 ml of distilled water. This solution is added to 1 ml of modified BSA solution (10 mg/ml). The mixture is incubated for 3 hours at room temperature and 18 hours at 4° C., and several extensive dialyses are then performed against 0.1M phosphate buffer pH 7.0.

The test with radiolabelled cysteine is carried out again on the protein after coupling of the peptide. Determination of the number of unmodified maleimide groups indicates by difference a degree of substitution of 7 mol of peptide (VI) per mole of BSA.

Two other immunogenic conjugates using Limulus polyphemus haemocyanin (LPH) and human transferrin (SIGMA) as carrier proteins were prepared under the same conditions.

D) Preparation of anti-Ang III antibody (or antiserum).

The animal used is the New Zealand breed rabbit. The first immunisation consists in injecting 1 mg of immunogen intradermally in the presence of Freund's complete adjuvant. Boosters are performed subcutaneously at 1-month intervals with the same quantity of immunogen in the presence of Freund's complete adjuvant.

E) Determination of the titre of the anti-Ang III sera.

100 µl of a dilution of rabbit serum in 0.1M imidazole-HCl buffer pH 7.4+0.2% BSA are incubated in the presence of 100 µl of iodine-125-labelled Ang III having a specific activity of 74 TBq/mmol (Amersham), providing 5000 cpm.

Separation of the Ang III bound to the antibody from free Ang III is carried out by adding 1 ml of 20% polyethylene glycol 6000 (PEG) and 100 µl of solution of bovine globulins containing 10 mg/ml. After centrifugation, the radioactivity of the pellet corresponding to Ang III bound to the antibody is measured. The technique used is that described by GREENWOOD, F. C. et al. (Biochem. J., 1963, 89, 114–118).

Rabbit serum binds at most 60% of the iodine-125-labelled Ang III.

F) Immunological characterisation of the anti-Ang III antiserum.

a) Evaluation of the immunoreactivity of the antiserum prepared with respect to Ang III.

100 µl of a dilute solution of the anti-Ang III antiserum (corresponding to approximately 50% of binding to iodinated Ang III) are incubated in the presence of 50 µl of free Ang III and 50 µl of iodinated Ang III providing 5000 cpm for 18 hours at 4° C. Separation of bound Ang III and free Ang III is carried out by polyethylene glycol precipitation. The iodinated Ang III-antibody binding is 50% displaced by adding 250 pg of Ang III. The antibody hence recognises Ang III.

b) Cross-reactions of the anti-Ang III antibody with Ang I and Ang II.

The cross-reaction of the anti-Ang III antibodies was measured with respect to Ang I and Ang II. The percentage is less than 1% for both peptides.

The anti-Ang III antibody may be used as obtained in the antiserum, or after purification on protein A-Sepharose.

EXAMPLE 2

Capacity for capture of Ang III by the anti-Ang III antibodies described above in the presence of anti-Ang II monoclonal antibody 4D8 and iodinated Ang II.

The antibody 4D8 is a mouse immunoglobulin; it is described in the proceedings of the congress "The Renin-Angiotensin System as a Therapeutic Target", Basle, 29–31 Oct. 1989, a SANOFI communication.

A solution containing the following is prepared:
100 µl of a solution of rabbit anti-Ang III antibody, obtained in Example 1,
50 µl of a solution of Ang III,
50 µl of a solution of iodinated Ang II (specific activity 74 TBq/mmol (Amersham)), providing 4000 cpm,
100 µl of a solution of anti-Ang II antibody (4D8), diluted in such a way that it binds only 30% of the iodinated Ang II.

The reaction volume is made up to 400 µl with the incubation buffer, namely imidazole-HCl (0.1M; pH 7.4) containing 0.2% of BSA. Incubation is carried out for 18 hours at +4° C.

A suspension of 500 µl of magnetic particles coated with antibodies directed towards mouse immunoglobulins (Amerlex M, marketed by Amersham) is added. Incubation is carried out for 15 minutes, the magnetic particles are then separated from the reaction medium using a magnet and the radioactivity contained in the magnetic phase is measured.

A series of measurements was carried out, varying the quantity of Ang III from 0 to 40 pg/test. Control tests were performed in the absence of anti-Ang III antibody.

Measurement of the radioactivity enables the results to be expressed as the ratio of the concentrations B/Bo of the (iodinated Ang II)-anti-Ang II antibody complex for each quantity of Ang III.

These results are recorded in Table 1.

TABLE 1

| | B/Bo (in p. cent) | |
|---|---|---|
| Ang III (pg/test) | in absence of anti-Ang III antibody | in presence of anti-Ang III antibody |
| 0 | 100 | 100 |
| 5 | 67 | 100 |
| 10 | 39 | 100 |
| 20 | 18 | 100 |
| 40 | 5 | 96 |

As shown by the results in Table 1, the binding of iodinated Ang II to the antibody 4D8 is decreased by adding Ang III; this binding is fully restored by the presence of anti-Ang III antibody.

In this experiment, it was, in addition, verified that the addition to the reaction medium of anti-Ang III antibody at the concentration used has no influence on the reaction of Ang II with the anti-Ang II antibodies.

EXAMPLE 3

Specific assay of Ang II in the presence of anti-Ang III antibody.

According to one of the embodiments described above, the kit used in this example comprises anti-Ang II monoclonal antibodies bound to a solid support.

More precisely, the antibodies are bound to the walls of a tube (Startube ® marketed by NUNC). The kit then consists of the following components:

NUNC Startube coated with anti-Ang II monoclonal antibodies 4D8 in such a way that 30% of the iodinated Ang II is bound,
solutions of Ang II, for the calibration, calibrated with respect to the Ang II international standard, batch 86/538, supplied by the Medical Research Council, a solution of Ang II labelled with iodine-125, of activity as defined in Example 2, a solution of rabbit anti-Ang III polyclonal antibody, prepared in Example 1 above and diluted in such a way that it enables at least 10 pg of Ang III per test to be captured.

The assay is carried out in imidazole-HCl buffer (0.1M; pH 7.4) containing 0.2% of BSA. The final reaction volume is 250 μl.

a) Calibration curve in the presence of 10 pg of Ang III.

100 μl of rabbit anti-Ang III polyclonal antibody are incubated with 50 μl of a solution of Ang III (corresponding to 10 pg of Ang III), 50 μl of a solution of Ang II standard and 50 μl of a solution of iodinated Ang II (4000 cpm) in the tube coated with monoclonal antibody 4D8 for 18 hours at +4° C.

The radioactivity is measured in the dry tubes after aspiration of the incubation medium and washing with 1 ml of imidazole-HCl buffer (0.1M; pH 7.4). The radioactivity is that of the anti-Ang II antibody-iodinated Ang II complex.

A calibration series was prepared by varying the quantities of Ang II from 0 to 40 pg/test. The measurement of radioactivity enables the results to be expressed as the concentration ratio B/Bo of the (iodinated Ang II)-anti-Ang II antibody complex for each quantity of Ang II (column 1).

10 pg of Ang III are added in each of the tests corresponding to the calibration curve (column 2), and the lowering of the ratio B/Bo due to the cross-reaction of the anti-Ang II antibody with the Ang III present is observed.

Lastly, in a third series of experiments (column 3, 10 pg of Ang III and anti-Ang III antibody are added in each of the tests corresponding to the calibration curve.

The results are recorded in Table 2 below.

TABLE 2

| Ang II (pg/test) | Column 1 B/Bo (p. cent) | Overload 10 pg Ang III B/Bo (p. cent) | |
|---|---|---|---|
| | | Column 2 in absence of anti-Ang III antibody | Column 3 in presence of anti-Ang III antibody |
| 0 | 100 | 23 | 100 |
| 1.25 | 84 | 21 | 86 |
| 2.5 | 81 | 22 | 83 |
| 5 | 67 | 22 | 66 |
| 10 | 47 | 18 | 49 |
| 20 | 29 | 12 | 36 |
| 40 | 17 | 11 | 21 |

It is observed that the presence of anti-Ang III antibody enables the values of the calibration curve to be recovered as a result of the specific capture of the Ang III in the reaction medium.

It was, moreover, verified, as in Example 2, that the addition of anti-Ang III antibody at the concentration used has no influence on the Ang II calibration curve.

b) Specific assay of Ang II from plasma.

The actual assay is performed on a human plasma extract, the extract being obtained according to the technique described by J. NUSSBERGER et al. in Hypertension, 1985 (reference cited), and then concentrated.

100 μl of rabbit anti-Ang III polyclonal antibody are incubated with 100 μl of solution of Ang II standard or of plasma extract to be assayed and 50 μl of a solution of iodinated Ang II (4000 cpm) in the tube coated with monoclonal antibody 4D8 for 18 hours at +4° C.

The radioactivity is measured in the dry tubes after aspiration of the incubation medium, as in Example 3 a).

A determination of the Ang II performed in the absence of anti-Ang III antibody leads to the determination of an apparent quantity of 81 pg in the test, while, in the presence of anti-Ang III antibody, only 57 pg are measured in the test. The difference results from the removal of the quantity of Ang III immunocaptured by the anti-Ang III antibodies.

It is deduced from this that the presence of Ang III leads in this case to an error of $$\frac{81-57}{57},$$

equivalent to 42%, in the direct determination of Ang II carried out using anti-Ang II antibody (4D8), as a result of the cross-reaction between this antibody and the Ang III. This error may be eliminated by means of the simultaneous use of the anti-Ang III antibody, which is one of the subjects of the present invention.

EXAMPLE 4

Preparation of anti-Ang I antibody.

The peptide (VII) in which $R_2$=Ahx and $R_3$=Asp is prepared, and the rabbit antiserum is then prepared by immunisation according to the method described in Example 1.

EXAMPLE 5

Preparation of anti-hexapeptide antibody.

The peptide (VIII) in which $R_1$=Pro and $R_2$=Ahx is prepared using the method described in Example 1, step A.

The antibody (rabbit antiserum) is then prepared using the method described in Example 1, steps B, C and D, and thereafter characterised.

EXAMPLE 6

Preparation of anti-pentapeptide antibody.

The procedure is as in the previous example for preparing the peptide (IX) in which $R_1$=Pro and $R_2$=Ahx, and the rabbit antiserum is then prepared by immunisation using the method described in Example 1, and thereafter characterised.

EXAMPLE 7

Capacity for capture of pentapeptide by the anti-pentapeptide antibodies prepared in Example 4, in the presence of anti-Ang II 4D8 and iodinated Ang II.

A solution containing the following is prepared:

100 μl of a solution of anti-pentapeptide antibody, prepared in Example 5,

100 μl of a solution of pentapeptide,

50 μl of a solution of iodinated Ang II (specific activity 74 TBq/mmol (Amersham)), providing 4000 cpm, and is placed in a tube coated with antibody according to Example 3.

The final dilution of anti-pentapeptide antibody is 1/25. Incubation is carried out for 18 hours at 4° C. The radioactivity is measured in the dry tubes after aspiration of the incubation medium and washing with 1 ml of imidazole-HCl buffer (0.1M; pH 7.4). The radioactivity is that of the anti-Ang II antibody-iodinated Ang II complex.

The procedure is then as in Example 2, and the results recorded in Table 3 below are obtained:

TABLE 3

| Pentapeptide (pg/test) | B/Bo (in p. cent) | |
|---|---|---|
| | in absence of anti-pentapeptide antibody | in presence of anti-peptapeptide antibody |
| 0 | 100 | 100 |
| 1.25 | 95 | 100 |
| 2.5 | 92 | 100 |
| 5 | 75 | 100 |
| 10 | 69 | 100 |
| 20 | 48 | 97 |

EXAMPLE 8

Specific assay of Ang II in the presence of anti-Ang II antibody and anti-pentapeptide antibody.

According to one of the embodiments described above, the kit used in this example comprises anti-Ang II monoclonal antibodies bound to a solid support.

More precisely, the antibodies are bound to the walls of a tube (Startubex marketed by NUNC). The kit then consists of the following components:

NUNC Startube coated with anti-Ang II monoclonal antibodies 4D8 in such a way that 30% of the iodinated Ang II is bound, solutions of Ang II, for the calibration, calibrated with respect to the Ang II international standard, batch 86/538, supplied by the Medical Research Council, a solution of Ang II labelled with iodine-125, of activity as defined in Example 2, a solution of rabbit anti-Ang III polyclonal antibody, prepared in Example 1 above and diluted in per test to be captured, a solution of rabbit anti-peptapeptide polyclonal antibody prepared in Example 5 above, such as to enable at least 10 pg of pentapeptide per test to be captured.

The assay is carried out in imidazole-HCl buffer (0.1M; pH 7.4) containing 0.2% of BSA. The final reaction volume is 250 µl.

The calibration curve was established in the presence of 4 pg of Ang III and 4 pg of pentapeptide.

100 µl of a solution of rabbit anti-Ang III polyclonal antibody and anti-pentapeptide are incubated with 50 µl of a solution of Ang III and pentapeptide (corresponding to 4 pg of each peptide), 50 µl of a solution of Ang II standard and 50 µl of a solution of iodinated Ang II (4000 cpm) in the tube coated with monoclonal antibody 4D8 for 18 hours at +4° C.

The radioactivity is measured in the dry tubes after aspiration of the incubation medium and washing with 1 ml of imidazole-HCl buffer (0.1M; pH 7.4). The radioactivity is that of the anti-Ang II antibody-iodinated Ang II complex.

A calibration series was prepared by varying the quantities of Ang II from 0 to 40 pg/test. The measurement of radioactivity enables the results to be expressed as the concentration ratio B/Bo of the (iodinated Ang II)-anti-Ang II antibody complex for each quantity of Ang II (column 1).

4 pg of Ang III and 4 pg of pentapeptide are added in each of the tests corresponding to the calibration curve (column 2), and the lowering of the ratio B/Bo due to the cross-reaction of the anti-Ang II antibody with the Ang III and the pentapeptide present is observed.

Lastly, in a third series of experiments (column 3), 4 pg of Ang III, 4 pg of pentapeptide and the anti-Ang III and anti-pentapeptide antibodies are added in each of the tests corresponding to the calibration curve.

The results are recorded in Table 4 below:

TABLE 4

| | | Overload 4 pg Ang III 4 pg Ang 4–8 B/Bo (p. cent) | |
|---|---|---|---|
| Ang II (pg/test) | Column 1 B/Bo (p. cent) | Column 2 in absence of anti-Ang III and anti-Ang 4–8 antibodies | Column 3 in presence of Anti-Ang III and anti-Ang 4–8 antibodies |
| 0 | 100 | 53 | 100 |
| 2.5 | 85 | 47 | 87 |
| 5 | 72 | 44 | 73 |
| 10 | 56 | 34 | 55 |
| 20 | 38 | 27 | 38 |
| 40 | 22 | 19 | 25 |

It is observed that the presence of anti-Ang III and anti-pentapeptide antibodies enables the values of the calibration curve to be recovered as a result of the specific capture of the Ang III and the pentapeptide in the reaction medium.

It was, moreover, verified, as in Example 2, that the addition of anti-Ang III and anti-pentapeptide antibodies at the concentration used has no influence on the Ang II calibration curve.

We claim

1. A kit for the specific assay of Angiotensin II, comprising:
    (a) an anti-Angiotensin II antibody,
    (b) a solution of labelled Angiotensin II, and
    (c) a solution of anti-Angiotensin III antibody, said anti-Angiotensin III antibody exhibiting a cross-reactivity with Angiotensin II of less than 10%.

2. A kit according to claim 1, wherein said Angiotensin II is labelled with an enzyme.

3. A kit according to claim 2, which further comprises a solution containing a substrate for said enzyme labelling said Angiotensin II.

4. A kit according to claim 3, further comprising a reagent for visualizing the activity of said enzyme and a solution capable of stopping the reaction of said enzyme and said substrate.

5. A kit according to claim 1, wherein said Angiotensin II is labelled with a label selected from the group consisting of a fluorescent compound, a luminescent compound and a radioisotope.

6. A kit according to claim 1, wherein said Angiotensin II antibody is monoclonal.

7. A kit according to claim 1, wherein said Angiotensin II antibody is in solution.

8. A kit according to claim 1, wherein said Angiotensin II antibody is bound to a solid support.

9. A kit according to claim 8, wherein said solid support is a tube, a microtitration plate or particles.

10. A kit according to claim 9, wherein said particles are magnetic.

11. A kit according to claim 1, wherein said anti-Angiotensin III antibody is a monoclonal antibody.

12. A kit according to claim 1, wherein said anti-Angiotensin II antibody is a polyclonal rabbit antiserum.

13. A kit according to claim 1, wherein said anti-Angiotensin III antibody exhibits a crossreactivity with Angiotensin II of less than 5%.

14. A kit according to claim 1, further comprising at least one additional antibody selected from the group consisting of an anti-Angiotensin I antibody, an antibody that binds to hexapeptide IV and an antibody that binds to pentapeptide V, wherein each said additional antibody exhibits a cross-reactivity with Angiotensin II of less than 10%.

15. A kit according to claim 14, wherein each said additional antibody exhibits a crossreactivity with Angiotensin II of less than 5%.

16. A kit according to claim 14, wherein said additional antibody is a monoclonal antibody.

17. A kit according to claim 14, wherein said additional antibody is a polyclonal rabbit antiserum.

18. A kit according to claim 1, further comprising a plurality of standard solutions each including a different predetermined amount of Angiotensin II, said amount being greater than or equal to zero.

19. A kit according to claim 1, further comprising a washing solution.

20. A kit according to claim 1, wherein said anti-Angiotensin II antibody is polyclonal.

21. A kit according to claim 1, wherein said anti-Angiotensin III antibody is obtained by immunization of an animal with a peptide derivative of formula (amino acids 1-7 or 2-7 or 3-7 of SEQUENCE ID NO. 2)

$$H\text{-}X_1\text{-}Tyr\text{-}Ile\text{-}His\text{-}R_1\text{-}R_2\text{-}Cys\text{-}NH_2$$

in which
$R_1$ denotes a direct bond or a chain-link comprising 1 or 2 natural amino acids,
$R_2$ denotes a group of formula $-NH-(CH_2)_n-CO-$,
n denotes an integer from 1 to 9, and
$X_1$ denotes a dipeptide Arg-Val residue.

22. A kit according to claim 21, further comprising
(d) at least one additional antibody selected from the group consisting of (i) an anti-Angiotensin I antibody obtained by immunization of an animal with a peptide derivative of formula (SEQUENCE ID NO. 3) H-Cys-$R_2$-$R_3$-Arg-Val-Tyr-Ile-His-Pro-Phe-His-Leu-OH in which
$R_3$ denotes a direct bond or a chain-link comprising 1 or 2 natural amino acids,
$R_2$ denotes a group of formula $-NH-(CH_2)_n-CO-$, and
n denotes an integer from 1 to 9 inclusive, (ii) an anti-pentapeptide antibody obtained by immunization of an animal with a peptide derivative of formula (amino acids 1-7 or 2-7 or 3-7 of SEQUENCE ID NO. 2) H-$X_1$-Tyr-Ile-His-$R_1$-$R_2$-Cys-$NH_2$ in which
$R_1$ denotes a direct bond or a chain-link comprising 1 to 2 natural amino acids,
$R_2$ denotes a group of formula $-NH-(CH_2)_n-CO-$,
n denotes an integer from 1 to 9 inclusive, and
$X_1$ denotes a direct bond, and (iii) an anti-hexapeptide antibody obtained by immunization of an animal with a peptide derivative of formula (amino acids 1-7 or 2-7 or 3-7 of SEQUENCE ID NO. 2) H-$X_1$-Tyr-Ile-His-$R_1$-$R_2$-Cys-$NH_2$ in which
$R_1$ denotes a direct bond or a chain-link comprising 1 or 2 natural amino acids,
$R_2$ denotes a group of formula $-NH-(CH_2)_n-CO-$,
n denotes an integer from 1 to 9 inclusive, and
$X_1$ denotes a valine residue, said additional antibody exhibiting a crossreactivity with Angiotensin II of less than 10%.

23. A kit according to claim 22, wherein said anti-Angiotensin III exhibits a crossreactivity with Angiotensin II of less than 5%.

24. A kit according to claim 22, wherein said additional antibody exhibits a crossreactivity with Angiotensin II of less than 5%.

25. A kit according to claim 21, wherein said anti-Angiotensin II antibody exhibits a crossreactivity with Angiotensin II of less than 5%.

26. An anti-Angiotensin III antibody obtained by immunization of an animal with a peptide derivative of formula (amino acids 1-8 of SEQUENCE ID NO. 2)

$$H\text{-}Arg\text{-}Val\text{-}Tyr\text{-}Ile\text{-}His\text{-}R_1\text{-}R_2\text{-}Cys\text{-}NH_2$$

in which
$R_1$ denotes a direct bond or a chain-link comprising 1 or 2 natural amino acids,
$R_2$ denotes a group of formula $-NH-(CH_2)_n-CO-$, and
n denotes an integer from 1 to 9 inclusive,
wherein said peptide derivative is bound to a carrier protein, and wherein said anti-Angiotensin III antibody is specific for Angiotensin III and exhibits a cross-reactivity with Angiotensin II of less than 10%.

27. An anti-Angiotensin III antibody according to claim 26, wherein in said peptide derivative
$R_1$ denotes Pro or Pro bound to another natural amino acid, and n=5.

28. An anti-angiotensin III antibody according to claim 27, which is a polyclonal rabbit antiserum and which exhibits a crossreactivity with Angiotensin II of less than 1%.

29. An anti-Angiotensin III antibody according to claim 13, wherein said anti-Angiotension III antibody exhibits a crossreactivity with Angiotensin II of less than 5%.

30. An anti-pentapeptide antibody obtained by immunization of an animal with a peptide derivative of formula (amino acids 3-8 of SEQUENCE ID NO. 2)

H-Tyr-Ile-His-$R_1$-$R_2$-Cys-$NH_2$ in which
$R_1$ denotes a direct bond or a chain-link comprising 1 or 2 natural amino acids,
$R_2$ denotes a group of formula —NH—($CH_2$-$)_n$—CO—, and
n denotes an integer from 1 to 9 inclusive,
wherein said peptide derivative is bound to a carrier protein, and wherein said anti-pentapeptide antibody is specific for a degradation pentapeptide having all but the two N-terminal amino acid residues of Angiotensin III, and exhibits a crossreactivity with Angiotensin II of less than 10%.

31. An anti-pentapeptide antibody according to claim 30, wherein in said peptide derivative
$R_1$ denotes Pro or Pro bound to another natural amino acid, and n=5.

32. An anti-pentapeptide antibody according to claim 31, wherein said anti-pentapeptide antibody exhibits a crossreactivity with Angiotensin II of less than 1%.

33. An anti-pentapeptide antibody according to claim 30, wherein said anti-pentapeptide antibody exhibits a crossreactivity with Angiotensin II of less than 5%.

34. An anti-hexapeptide antibody obtained by immunization of an animal with a peptide derivative of formula (amino acids 2-8 of SEQUENCE ID NO. 2)

H-Val-Tyr-Ile-His-$R_1$-$R_2$-Cys-$NH_2$ in which
$R_1$ denotes a direct bond or a chain-link comprising 1 or 2 natural amino acids,
$R_2$ denotes a group of formula —NH—($CH_2$-$)_n$—CO—, and
n denotes an integer from 1 to 9 inclusive,
wherein said peptide derivative is bound to a carrier protein, and wherein said anti-hexapeptide antibody is specific for a degradation hexapeptide having all but the N-terminal amino acid residue of Angiotensin III, and exhibits a cross-reactivity with Angiotensin II of less than 10%.

35. An anti-hexapeptide antibody according to claim 34, wherein in said peptide derivative
$R_1$ denotes Pro or Pro bound to another natural amino acid, and n=5.

36. An anti-hexapeptide antibody according to claim 34, wherein said anti-hexapeptide antibody exhibits a crossreactivity with Angiotensin II of less than 5%.

37. An anti-Angiotensin I antibody obtained by immunization of an animal with a peptide derivative of formula (SEQUENCE ID NO. 3):

H-Cys-$R_2$-$R_3$-Arg-Val-Tyr-Ile-His-Pro-Phe-His-Leu-OH in which
$R_3$ denotes a direct bond or a chain-link comprising 1 or 2 natural amino acids,
$R_2$ denotes a group of formula —NH—($CH_2$-$)_n$—CO—, and
n denotes an integer from 1 to 9 inclusive,
wherein said peptide derivative is bound to a carrier protein, and wherein said anti-Angiotensin I antibody is specific for Angiotensin I and exhibits a cross-reactivity with Angiotensin II of less than 10%.

38. An anti-Angiotensin I antibody according to claim 37, wherein in said peptide derivative
$R_3$ denotes Asp or Asp bound to another natural amino acid, and n=5.

39. An anti-Angiotensin I antibody according to claim 37, wherein said anti-Angiotensin I antibody exhibits a cross-reactivity with Angiotensin II of less than 5%.

40. A method for the assay of Angiotensin II which comprises the steps of:
a) incubating
i) an anti-Angiotensin II antibody with a reaction medium comprising
ii) an extract of a biological fluid,
iii) labeled Angiotensin II, and
iv) an anti-Angiotensin III antibody which is specific for Angiotensin III and exhibits a crossreactivity with Angiotensin II of less than 10%, at a temperature between 4° C. and room temperature for 12 to 72 hours;
b) separating labeled and unlabeled Angiotensin II bound to said anti-Angiotensin II antibody from said reaction medium; and
c) measuring the amount of labeled Angiotensin II bound to said anti-Angiotensin II antibody to determine the amount of unlabeled Angiotensin II present in said extract.

41. A method according to claim 40, wherein said anti-Angiotensin II antibody is bound to particles.

42. A method according to claim 41, wherein said particles are magnetic.

43. A method according to claim 40, wherein said extract is a plasma extract.

44. A method according to claim 40, wherein said anti-Angiotensin III antibody is obtained by immunization of an animal with a peptide derivative of formula (amino acids 1-8 of SEQUENCE ID NO. 2)

H-Arg-Val-Tyr-Ile-His-$R_1$-$R_2$-Cys-$NH_2$ in which
$R_1$ denotes a direct bond or a chain-link comprising 1 or 2 natural amino acids,
$R_2$ denotes a group of formula —NH—($CH_2$-$)_n$—CO—, and
n denotes an integer from 1 to 9 inclusive,
wherein said peptide derivative is bound to a carrier protein.

45. A method according to claim 40, wherein said reaction medium further comprises: (v) one or more antibodies selected from this group consisting of an antibody that binds to pentapeptide V, an antibody that binds to hexapeptide IV and an anti-Angiotensin I antibody, wherein each of said one or more antibodies exhibit a cross-reactivity with Angiotensin II of less than 10%.

46. A method according to claim 40, wherein said determination in step c) is effected by reference to a calibration curve.

47. A method according to claim 46, wherein said calibration curve is obtained by:
 (A) incubating
  i) an anti-Angiotensin II antibody with a plurality of reaction media each comprising
  ii) an solution including a different predetermined amount of Angiotensin II, said amount being greater than or equal to zero,
  iii) said labeled anti-Angiotensin II, and
  iv) said anti-Angiotensin III antibody, at a temperature between 4° C. and room temperature for 12 to 72 hours;
 (B) separating said Angiotensin II bound to said anti-Angiotensin II antibody from said Angiotensin II remaining unbound; and
 (C) measuring the amount of labeled Angiotensin II bound to said anti-Angiotensin II antibody in each of said plurality of reaction media and relating each said amount to the amount of unlabeled Angiotensin II employed in the respective reaction medium to yield said calibration curve.

48. An antibody that binds to hexapeptide IV, wherein said antibody exhibits a cross-reactivity with Angiotensin II of less than 10%.

49. An antibody that binds to pentapeptide V, wherein said antibody exhibits a cross-reactivity with Angiotensin II of less than 10%.

* * * * *

UNITED STATES PATENT AND TRADEMARK OFFICE
CERTIFICATE OF CORRECTION

PATENT NO. : 5,296,354                            Page 1 of 3
DATED      : March 22, 1994
INVENTOR(S) : SIMON et al.

It is certified that error appears in the above-indentified patent and that said Letters Patent is hereby corrected as shown below:

On the title page, item [75] Inventors:

"Saint Nazair du Pezan" should read --Saint Nazaire du Pezan--.

Column 1, lines 6-8 and 10, "angiotension" should read --angiotensin--.

Column 2, line 29, "$10^{-11}$ $M^{1}$" should read --$10^{\pm 11}$ $M^{1}$--.

Column 4, line 56, insert --the-- before "Ang I".

UNITED STATES PATENT AND TRADEMARK OFFICE
CERTIFICATE OF CORRECTION

PATENT NO. : 5,296,354
DATED : March 22, 1994
INVENTOR(S) : SIMON et al.

It is certified that error appears in the above-indentified patent and that said Letters Patent is hereby corrected as shown below:

Column 7, line 42, delete ")" after "3-8".

Column 7, line 55, "amino acids 1-7 or 2-7 or 3-7" should read --1-8, 2-8 or 3-8--.

Column 7, line 58 "H-$X_1$-Tyr-Ile-His-$R_1$-Cys-NH2" should read --H-$X_1$-Tyr-Ile-His-$R_1$-$R_2$-Cys-$NH_2$--.

Column 11, line 34, insert --)-- after "column 3".

Column 13, line 23, "Startubex" should read --Startube®--.

Column 13, line 34, before "per" insert --such a way that it enables at least 10 pg of Ang III--.

Claims 6, 7 and 8, column 17, lines 12, 14 and 16, insert --anti--- before "Angiotensin II".

UNITED STATES PATENT AND TRADEMARK OFFICE
CERTIFICATE OF CORRECTION

PATENT NO. :   5,296,354
DATED       :   March 22, 1994
INVENTOR(S) :   Simon, et al It is certified that error appears in the above-indentified patent and that said Letters Patent is hereby corrected as shown below:

Claim 23, column 18, line 40, after "Angiotensin III" insert --antibody--.

Claim 25, column 18, line 46, "II" should read --III--.

Claim 29, column 19, line 6, "13" should read --26--; "Angiotension" should read --Angiotensin--

Claim 45, column 20, line 62, "this" should read --the--

Claim 47, column 21, line 9, "an" should read --a--; column 21, line 12, delete "said"; column 21, line 13, "said" should read --an--.

Signed and Sealed this

Ninth Day of January, 1996

BRUCE LEHMAN

*Attest:*

*Attesting Officer*          *Commissioner of Patents and Trademarks*

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Homo sapiens ( v i i ) IMMEDIATE SOURCE:
        ( B ) CLONE: Angiotensin I -continued (x i) SEQUENCE DESCRIPTION: SEQ ID NO:1:

Asp Arg Val Tyr Ile His Pro Phe His Leu
1               5                       10

(2) INFORMATION FOR SEQ ID NO:2:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (vii) IMMEDIATE SOURCE:
        (B) CLONE: Anti-Ang III antibody immunogen (ix) FEATURE:
        (A) NAME/KEY: Modified-site
        (B) LOCATION: 6..7
        (D) OTHER INFORMATION: /label=Xaa
            / note="A direct bond or chain-link comprising 1
            or 2 natural amino acids."

(ix) FEATURE:
        (A) NAME/KEY: Modified-site
        (B) LOCATION: 7..8
        (D) OTHER INFORMATION: /label=Xaa
            / note="A group of formula
            - NH- $(CH_2)_n$-CO-, in which n varies
            between 1 and 9."

(x i) SEQUENCE DESCRIPTION: SEQ ID NO:2:

Arg Val Tyr Ile His Xaa Xaa Cys
1               5

(2) INFORMATION FOR SEQ ID NO:3:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (iii) HYPOTHETICAL: NO (vii) IMMEDIATE SOURCE:
        (B) CLONE: Anti-Ang I antibody immunogen (ix) FEATURE:
        (A) NAME/KEY: Modified-site
        (B) LOCATION: 2..3
        (D) OTHER INFORMATION: /label=Xaa
            / note="A group of formula
            - NH- $(CH_2)_n$-CO-, in w;hich n varies
            between 1 and 9."

(ix) FEATURE:
        (A) NAME/KEY: Modified-site
        (B) LOCATION: 3..4
        (D) OTHER INFORMATION: /label=Xaa
            / note="A direct bond or a chain-link comprising 1
            or 2 natural amino acids."

(x i) SEQUENCE DESCRIPTION: SEQ ID NO:3:

Cys Xaa Xaa Arg Val Tyr Ile His Pro Phe His Leu
1               5                       10